United States Patent [19]

Lévêque et al.

[11] Patent Number: 4,480,921
[45] Date of Patent: Nov. 6, 1984

[54] APPARATUS TO REGISTER THE QUANTITY OF SEBUM SECRETED BY A SKIN

[75] Inventors: Jean-Luc Lévêque, Montfermeil; Gilbert Gras, Aulnay sous Bois, both of France

[73] Assignee: L'Oreal, Paris, France

[21] Appl. No.: 27,717

[22] Filed: Apr. 6, 1979

Related U.S. Application Data

[63] Continuation-in-part of Ser. No. 844,038, Oct. 20, 1977, abandoned.

[30] Foreign Application Priority Data

Feb. 5, 1979 [FR] France .............................. 79 02935

[51] Int. Cl.³ .............................................. G01J 3/45
[52] U.S. Cl. ................................................... 356/434
[58] Field of Search ...................... 356/434, 433, 432; 250/214 B, 214 DC

[56] References Cited

U.S. PATENT DOCUMENTS

| | | | |
|---|---|---|---|
| 3,013,467 | 12/1961 | Minsky | 356/432 |
| 3,711,210 | 1/1973 | Krukowski | 356/438 |
| 3,817,632 | 6/1974 | Picunko et al. | 356/434 |
| 3,887,281 | 6/1975 | Kurita et al. | 356/434 |
| 3,927,317 | 12/1975 | Liedholz | 356/434 |
| 4,027,981 | 6/1977 | Steinbatz | 356/434 |
| 4,035,087 | 7/1977 | Mori et al. | 356/434 |

FOREIGN PATENT DOCUMENTS

1959612  6/1971  Fed. Rep. of Germany ...... 356/432

Primary Examiner—R. A. Rosenberger
Attorney, Agent, or Firm—Brisebois & Kruger

[57] ABSTRACT

Method and apparatus to measure the quantity of sebum secreted by the skin, by passing light through the specimen. The light passed through the specimen is modulated at a predetermined frequency, and only light of the same modulated frequency is measured by a receiver. The apparatus includes automatic zero calibration, and several embodiments of stabilized phototransistor circuits.

12 Claims, 5 Drawing Figures

APPARATUS TO REGISTER THE QUANTITY OF SEBUM SECRETED BY A SKIN

This is a continuation in part of copending application Ser. No. 844,038 filed Oct. 20, 1977, now abandoned and is related to application in France Ser. No. 76-31524, filed Oct. 20, 1976, and its first and second certificates of addition and any disclosures thereof are incorporated herein by reference.

One knows that it is often necessary to evaluate optical characteristics, such as transparency, translucency, or reflection, of a sample. This is the case, in particular, when one takes comparative measurements to determine or register the quantity of sebum deposited on a ground glass support by the skin of a subject under study. To obtain exactly reproducible measurements, one was led, until now, to use a luminous flux as monochromatic as possible and to avoid the effects due to parasitical radiations, for example, to ambient light or to heat sources transmitting infrared rays. This technique necessitates operating in a black or closed chamber.

According to this technique, one has already proposed devices for comparatively measuring the secretion of sebum from skin by applying a thin plate of ground glass or a ground microscope slide on an area of the skin and examining the transparency of the slide with an essentially monochromatic beam emitted by a spectrophotometer: the "sebumeter" devices constructed according to this principal comprise in general an emission lamp, for example, a mercury vapor lamp, a prism monochromator or a diffraction grating for separating an extended emission range into a small range of wave lengths, and a photomultiplier. The devices constructed according to this technique are cumbersome and expensive; they permit measuring or registering the quantities of sebum secreted by an area of skin, being given that there is a correlation between, on the one hand, the transparency of the ground slide undergoing examination and previously applied on the area of skin to be studied for a period of time and with a certain pressure, and on the other hand, the quantity of sebum deposited on the slide.

A simplified device designed to register the quantity of sebum emitted by an area of skin has been previously proposed. In this device, a non-monochromatic luminous flux produced by a light bulb is sent to a translucent film which has been applied on the area of skin to be studied and the flux transmitted through the film is received on a photo-diode inserted in a circuit with a milliamperemeter powered by a battery. This device is constructed much more simply than the spectrophotometers previously used but it has the disadvantage of not providing exactly reproducible or repeatable measurements, partly because of aging of the lamp transmitting the luminous flux and partly because of the variation in output of the milliamperemeter circuit battery.

The present invention has as an object a device of simple construction, less cumbersome and of lower cost than prior devices to carry out a comparative measure of the secretion of sebum in an area of skin based on the correlation which exists between the quantity of sebum secreted and the transparency of a translucent slide applied for a period of time and with a given pressure on the area of skin to be studied. One of the essential advantages of the device according to the invention rests in the fact that the comparative measurement can be carried out without isolating the emitter means, the receiver means, and the translucent element being studied from ambient parasitical radiations such as ambient light or nearby sources of heat, for example. The device according to the invention can use a non-monochromatic luminous flux, for example a flux obtained from one or several electroluminescent diodes.

The present invention has then as an object the new industrial product which constitutes an apparatus for measuring or registering the quantity of sebum secreted by an area of skin of a living subject, in which an emitter furnishes a luminous flux in the direction of a translucent element previously applied in a predetermined fashion against the area of skin to be studied and in which a receiver measures the luminous flux transmitted from the emitter by transparency through the translucent element, the interpretation of the measurement being made by comparison of the measurement obtained with a standard for the translucent specimen, characterized by the fact that the emitter of flux furnishes a beam modulated at a fixed frequency, the receiver of luminous flux only measuring the flux received which has the frequency of modulation of the emitter.

In a first embodiment the output of the signal furnished by the flux receptor is through a filter stage including an adjuster for the level of its output voltage the filter stage feeding a digital voltmeter to indicate or read the result of the measurement. The level adjustment thus provided, permits the initial adjustment or calibration of the apparatus by setting a zero reading on the digital voltmeter when the glass plate subjected to the reading is a plate which did not have a deposit of sebum. However, once made this initial adjustment can no longer be modified and it is noted that this constitutes a disadvantage during the use of the apparatus. In effect, the zero reading established by the initial calibration or adjustment, as is evident, is a function of the glass plate used as a support for the sebum and, as a result, if for some reason, one decided to change the glass plate, the zero readings would not be the same, and it would then be necessary to establish a value for the plate carrying the sebum, and to subtract the corresponding value for the plate without the sebum. In addition, it has been found that the apparatus could drift caused, for example, by a large change in the temperature, or a variation in the supply voltages in these cases this drift means that the reading of zero is no longer obtained for a glass plate without sebum, so that one again must make a subtraction to obtain the resultant value as above indicated, with the complementary difficulty that the value to be subtracted is not necessarily always the same. Also, it has been verified that, when using this type of apparatus, the cleaning of the glass plates, between two successive uses, was especially difficult since cleaning in the usual way left on the glass a residue of sebum. In this case, it is likewise necessary to take into account, by subtraction, the value read for the glass plate used before the amount of sebum to be measured is deposited on the same plate. It has been verified that this step of subtraction, which it has been necessary to carry out in all the previous cases, is very disaggreable for the user and that it is thus very important to find a solution to this difficulty.

The present invention has as a further object to provide a second embodiment which includes a device (also usable with the first embodiment), this device permitting an automatic correction of the zero reading, a correction which the user could make with the ground glass plate on which the sebum is to be deposited, before the sebum is deposited. With this device according to the invention, the user places the plate in the apparatus, presses a zero reset button, and retrieves the plate. Then the sebum is deposited by application of the plate for a determined time duration and pressure on the area of skin to be studied. Then the plate is replaced in the apparatus to read directly the resultant value on the digital voltmeter of the apparatus. It is therefore apparant that the use of the apparatus according to the invention is greatly facilitated by this device to set to zero automatically.

The present invention, in consequence, has as an object a new industrial product which constitutes an apparatus to measure the quantity of sebum secreted by an area of skin of a living subject, in which an emitter supplies a luminous flux in the direction of a translucent element previously applied in a predetermined manner against the area of skin to be studied and in which a receptor measures the luminous flux transmitted from the emitter by transparency through the translucent element, the interpretation of the measurement being made by comparison with a measurement obtained for a reference standard of the translucency, the flux emitter supplying a light beam at a fixed frequency and the flux receptor being associated with a circuit to measure only the flux received which is at the frequency of modulation of the emitter and providing a measuring voltage which is a function of the received flux, characterized by the fact that the measured voltage of the reference is remembered and stored as desired and sent through a differential amplifier which subtracts if from the voltage of the following measurement to furnish a voltage resulting in a precise reading of the measured value.

In a preferred embodiment, the differential amplifier is connected to a terminal supplying the measuring voltage on one hand, directly, and, on the other hand, through the intermediary of a memory stage controlled by the user; the memory stage including a double analog/digital and digital/analog converter which permanently records on input the measured voltage and permanently restores on output, a reference voltage corresponding to a memorized binary value, the user being able to cause at will the replacement in the memory bank of the memorized value by a binary value corresponding to another measuring voltage received. The replacement in the memory bank of the value of the memorized voltage by a value corresponding to the measuring voltage received is accomplished by resetting to zero a binary counter with a pulse signal sent by the user, the pulse signal releasing an oscillator which sends to the meter (reset to zero), a number corresponding to the new measuring voltage received, a comparing device comparing the measuring voltage received and the output voltage which corresponds to the binary value set in the counter, and blocking the oscillator when equality if reached. It may be easily seen that the signal sent by the user to trigger the double converter may be furnished by a push-button and that the differential amplifier can output to a digital voltmeter.

In these embodiments the receptor of luminous flux is advantageously a phototransistor. It is well known that the sensitivity or response of phototransistors is a function of the bias voltage existing between the collector and the emitter, this bias voltage being usually affected by the continuous current which phototransistors furnish as a function of the ambient luminosity. This response is also a function of variations of temperature. It has been established that it was desirable to remedy this disadvantage so that the value registered on the apparatus would be perfectly proportional to the quantity of sebum subjected to the measurement and would be wholly independent of temperature conditions. To achieve this, one can, according to this invention, use one solution, taken from a group of three possible solutions, giving approximately the same satisfactory results. Considering the comparable effectiveness of the three solutions, the simplest is preferred and is described first below.

The present invention has then, in consequence, equally as an object, apparatus such as that described above in which the phototransistor flux receptor has a biased base connected by a resistance to ground and by another resistance to a source voltage.

This mode of operation assumes, as for the variation which will follow, that a terminal for electrical connection of the base of the phototransistor is furnished by the transistor manufacturer. The supplying is done by the collector and the output voltage of the phototransistor is referenced between ground and the emitter by a resistor. With this circuit, the continuous component of the measurement is equal to the bias voltage of the base at about 0.6 volt (the difference between the voltage of the base and the voltage of the emitter); it is noted that the result obtained with this circuit is very satisfactory despite the simplicity of the circuit.

In one variation of the circuit proposed above, the common point of the two bias resistances is connected to the base by a resistance which is much smaller than the two bias resistances, and to the emitter by a condenser. In this variation, the continuous component of the measurement acts as described above for the first circuit while the supplementary resistance added in series with the base is much less than the bias resistances. On the other hand, the condenser reinjects at the junction point of the two bias resistances, the alternating component of all the voltage appearing on the emitter; now, the voltage of the emitter is always equal, with a difference of 0.6 volt, to the voltage of the base; consequently any purely alternating signal produced on the base gives rise to an equivalent signal of the same value (peak to peak) at the junction point of the bias resistances so that the additional resistance in series with the base is not traversed by any alternating current. Under these conditions, all the pulsed luminous flux which arrives at the base of the phototransistor will be converted into current in the phototransistor, no current being lost in the additional or bias resistances; as a result the sensitivity and response of this circuit is conserved for the pulsed signals, which was not the case in the first circuit above in which the luminous flux created a base current part of which gave rise to the current of the emitter and part of which traversed the bias resistances.

In a third circuit, the collector of the phototransistor is directly connected to the supply and its emitter is connected to the negative inverting input of an operational amplifier, whose other input is connected to ground, the inverting input being connected to the output of the operational amplifier by a resistance, the output voltage being measured at the output of the operational amplifier. In this case, the continuous voltage of the collector-emitter of the phototransistor is approximately equal, during operation, to the supply voltage and all the current of the phototransistor traverses the resistance connected to the operational amplifier. It is noted that once again the sensitivity or response of the phototransistor is held constant for a variable luminous flux. This last circuit is used when a phototransistor is chosen whose construction does not provide a base connection.

It is clear that the improvements described above, concerning the resetting to zero and the phototransistor wiring, can be used equally well in either embodiment of this invention.

In both embodiments, the translucent element is placed in front of a reflecting element, the emitter and the receiver both being placed on the opposite side of the translucent element from the abovementioned reflecting element. In each embodiment two coaxial fiber optics are used, of which one extremity is joined to an emitter-receiver and of which the other extremity is placed face to face with the translucent element subjected to the luminious flux; the peripheral or outer fiber optic is supplied by the emitter of flux and the central or inner fiber optic is joined to the flux receiver; the extremity of the double fiber optic which is not joined to the emitter-receiver, is placed opposite that surface of the translucent element which has been applied against the area of skin being studied, the other surface of the translucent element being applied against a mirror.

The translucent element receiving the luminous flux from the emitter can be a ground glass plate or a ground microscope slide; the luminous flux emitted by the emitter can be a non-monochromatic flux.

According to a first variation, the emitter of flux comprises a single emitter element whose emitted flux is in a narrow range of wave lengths distributed around a median wave length, the distribution of the wave lengths around the median wave length being essentially according to a Gaussian curve.

In another variation, the emitter of flux comprises a plurality of emitter elements and/or the receiver of flux comprises a plurality of receptor elements; in this case, the apparatus can advantageously comprise n emitter elements with parallel axes furnishing emissions in the same range of wave lengths, n being a whole number greater than 1, and n receiver elements, the measurements obtained from each receiver element being added to give a mean value for the entire area of the translucent element examined.

One can advantageously forsee that the photoreceiver can be equipped to follow the current without any amplification function; the receiver element can supply a variable gain amplifier tuned to the frequency of modulation of luminous flux emitted by the emitter element of corresponding flux; the variable gain amplifier can advantageously act as a low gain filter and be placed in series with a high gain filter; the variable gain amplifier is preferably followed by an amplification stage and a stage of rectification of the sinusoidal current; the output signal furnished by the flux receiver is from a filtering stage including an adjustment for the level of the output voltage.

One of the essential advantages of the apparatus of the invention comes from the fact that the modulation of luminous flux emitted and the tuning of the receiver to the frequency of modulation eliminates all effects of parasitical emissions due to ambient light or heat sources; the entire circuit of the apparatus of the invention functions, all or nothing, in synchronism with the flux emitter. Thus one obtains, without any isolating precautions from the ambient surroundings, an exactly reproducible measurment. The flux of the emitter varies very slowly over a period of time by aginf of the emitter but this variation is not of considerable significance, taking into consideration the fact that the measurements are comparative and suppose an initial adjustment of the apparatus beginning with a measurement made on a standard or reference translucent element.

To better understand the objects of the invention, two non-limiting embodiments of the invention, shown in the drawings, will now be described, by way of example.

Figure 1:
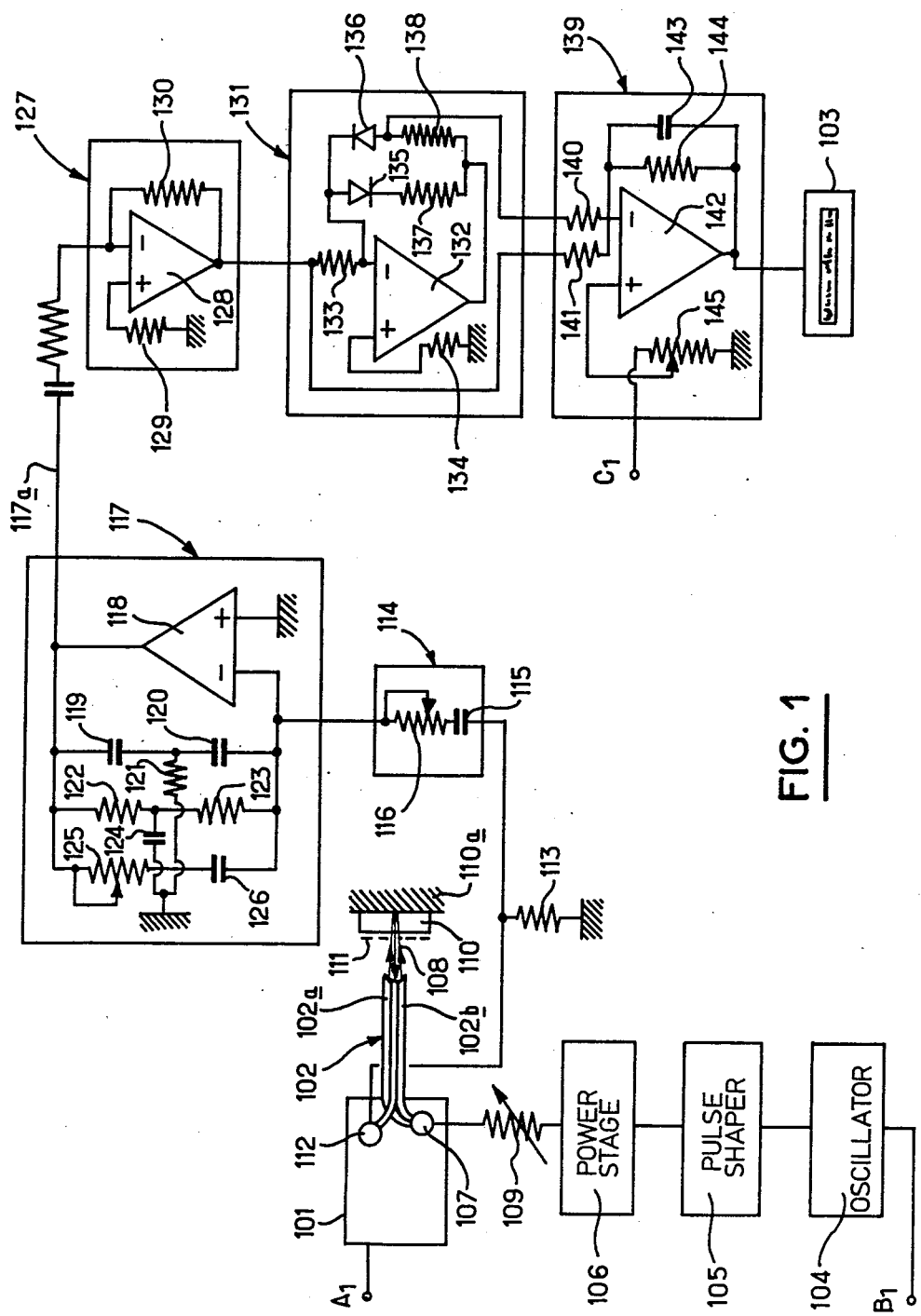
FIG. 1 shows schematically an apparatus according to a first embodiment of the invention.

The apparatus which is shown in FIG. 1, is intended to measure comparatively the quantity of sebum secreted by an area of skin. To do this, one applies on the area of skin being studied, in a known way for a predetermined period of time and at a determined pressure, a translucent plate, for example a microscopic slide, ground on one surface. This application of the plate against the skin causes a deposit of sebum on the plate which modifies the transparency of the plate. In the case of a plate of ground glass, one does this in such a way that the sebum is deposited on the ground surface of the plate. It is known that a correlation exists between the transparency of the plate and the quantity of sebum secreted per unit of time per area of skin studied; one then takes a first measurement by using as a standard a plate of ground glass, which has not been applied on the skin and one adjusts the apparatus in such a way that the measurement of the output current corresponds to an indication of zero. One then replaces the plate of ground glass with a plate of ground glass having been previously applied on the skin to be examined: this plate is more transparent than the reference standard and the luminous flux received by the receiver corresponds to a higher output current which is transformed into a positive numerical value given by comparison with the initial adjustment.

With reference to the drawing, particularly FIG. 1, there is shown apparatus according to the invention comprising an emitter-receiver unit 101, the output of the receiver being sent to a visual display means 103.

The emitter-receiver unit 101 is energized by an electric current from a power supply at 5 or 15 volts stabilized to approximately $5 \times 10^{-5}$ volts. The power supply is connected to and furnished at points $A_1$, $B_1$, and $C_1$ of the drawing. An oscillator 104 provides a sinusoidal signal at a selected frequency, for example 3.104 Khz. The oscillator 104 feeds a shaper circuit 105 which provides rectangular impulses at the same frequency as oscillator 104. The shaper circuit 105 feeds a power stage 106 which provides a current that can go as high as 80 milliamperes. An electroluminescent diode 107 which is part of the emitter-receiver unit, furnishes luminous flux 108 the intensity of which is adjustable by a rheostat 109. The luminous flux is modulated at the frequency of oscillator 104, and the intensity of the flux varies with the rectangular pulses. The emitter-receiver unit 101 also has a photodetecter 112 consisting of a phototransistor and is connected to a double optical fiber designated 102 as a whole.

The double optical fiber 102 consists of a peripheral fiber and a central fiber placed co-axially, each being able to direct luminous flux. The peripheral fiber 102a is connected at its end attached to unit 101 to the electroluminescent diode 107 and the central fiber 102b is connected at its end attached to unit 101 to phototransistor 112. The double optical fiber 102 has a free end, which is placed opposite a glass plate 110, having a ground side facing the end of optical fiber 102; on this ground side a certain amount of sebum, indicated on the drawing by dotted line 111, may or may not have been placed depending on whether an actual or a reference measurement is being made. The side of the glass plate 110, which does not have sebum 111, is placed against a flat mirror 110a. The end of fiber 102 is placed at a distance corresponding essentially to the position of maximum flux reception for a given emission. Actually it has been noted, when two co-axial fibers are used as described above, that the luminous flux measured by the phototransistor is, for a given emission, a function of the distance between the reflecting surface and the end of the two co-axial fibers, this function or curve having a maximum. To reduce the influence of an accidental variation in the distance between the end of the fibers and the mirror, the end of the fiber should be placed at a distance near the corresponding maximum of the curve. The luminous flux emitted by electroluminescent diode 107 is a non-monochromatic infra-red flux of an intensity of 40 mcd and the preferred distance from the end of fiber 102 to flat mirror 110a is 7 mm. With such spacing between the end of fiber 102 and the flat mirror 110a, one has about reached the maximum of the voltage-distance curve of the phototransistor for a double optical fiber such as that which is part of the emitter-receiver unit 201 and which is designated "S 322-3.L.E.D." by the manufacturers company "SKAN-A-MATIC".

The emitter of phototransistor 112 is connected to ground through a resistor 113. The signal from the emitter is fed to a high pass filter 114 which includes a serially connected capacitor 115 and an adjustable resistor 116. Condenser 115 has a value of 110 nano-Farads and resistor 116 has a value of approximately 470 Ohms. The filter 114 feeds the negative input of a variable gain amplifier assembly 117, the assembly 117 containing a subassembly including a resistor 125 and a capacitor 126 soon to be described in detail.

The subassembly 125, 126 functions as a low pass filter which, associated with high pass filter 114 does not permit passing to line 117a, currents other than those corresponding to a predetermined frequency. One tunes the filter 114 and the subassembly 125-126 in such a fashion that the frequency passed is the frequency of oscillator 104, so that on the output line 117a there is obtained a sinusoidal voltage corresponding to the first sinusoidal component of the rectangular pulse furnished by the phototransistor 112, and which has the frequency of oscillator 104.

Amplifier 117 includes an operational amplifier 118 whose negative input is connected to filter 114 and whose positive input is connected to ground. Between the negative input and the output of operational amplifier 118 there is connected in reverse feedback a double T filter tuned to the frequency of the oscillator 4 and including, for the first T, series connected capacitors 119 and 120 whose junction is connected to ground by a resistor 121, and for the second T, two resistors 122, 123 connected in series and whose junction point is connected to ground by a capacitor 124. It is evident from FIG. 1, that in amplifier assembly 117, between the negative input and the output of operational amplifier 118, there are the parallel paths of (a) capacitors 119, 120, (b) resistors 122, 123 and (c) the subassembly 125, 126 including variable resistor 125 of about 120K and capacitor 126 of 390 pico-Farad.

The output 117a is connected to the negative input of an amplifier assembly 127 containing an operational amplifier 128 whose positive input is connected to ground by a resistor 129 and whose output is connected to its negative input by a resistor 130. The amplifier 127 has a gain of 10 and the output goes to the input of a rectifier stage 131 for obtaining, in positive, the two alternations of the sinusoidal current furnished by amplifier 127. The rectifier stage is comprised of an operational amplifier 132 which receives the output of the amplifier 127 at its negative terminal through a resistor 133. The positive input terminal of operational amplifier 132 is connected to ground through resistor 134. Between the output and negative input of operational amplifier 132, there is connected a circuit comprising two parallel legs including respectively, a diode 135 and resistor 137, and a diode 136 and resistor 138. The two diodes 135 and 136 are connected to pass current through the legs in opposite directions. One output of stage 131 is taken from the junction between resistor 138 and the anode of diode 136. A second output of stage 131 is the same as its input from stage 127 and is taken from the input end of resistor 133.

The two output lines connect together in a filter stage assembly 139 through parallel connected resistors 140 and 141. The common output of resistors 140 and 141 is connected to the negative input of an operational amplifier 142 forming a part of filter stage 139. Between the negative input and the output of this operational amplifier 142 are connected in parallel, a condenser 143 and a resistor 144. The positive terminal of the operational amplifier 142 is connected to a regulated voltage power supply at terminal $C_1$ through a variable resistor 145. Adjusting variable resistor 145 adjusts the level of the operational amplifier 142 to a desired output voltage.

The output of filter stage 139 (the output of the operational amplifier 142) goes to a digital voltmeter which constitutes the display means 103 of the apparatus according to the invention. The adjustable resistor 145 permits obtaining a zero display on the display means 103 when the plate 110 is a plate without a deposit of sebum. In other words, the variable resistor 145 permits initial adjustment or leveling of the apparatus.

It is clear that the apparatus according to the invention permits comparative measurement of a deposit of sebum since there is a correlation between the transparency of the plate 110 and the quantity of sebum deposited on the plate. It is also clear that the modulation applied to the emission of the electroluminescent diode 107 frees the emission from all the parasitical emissions, including those corresponding to ambient light and to infra-red emissions from nearby heat sources. The measurement can be taken in open air, which considerably simplifies the measurements of "sebumetry". The device is, in addition, less cumbersome than prior devices and has a moderate cost. Finally, it has been ascertained that the device of the invention is very reliable and permits good reproducibility of the comparative measurements made.

In the embodiment described above, the electroluminescent diode 107 emits a luminous flux of red light but the choice of the mean or average wave length of the luminous flux emitted is not of critical importance for the performance of the apparatus of the invention.

Figure 1A:
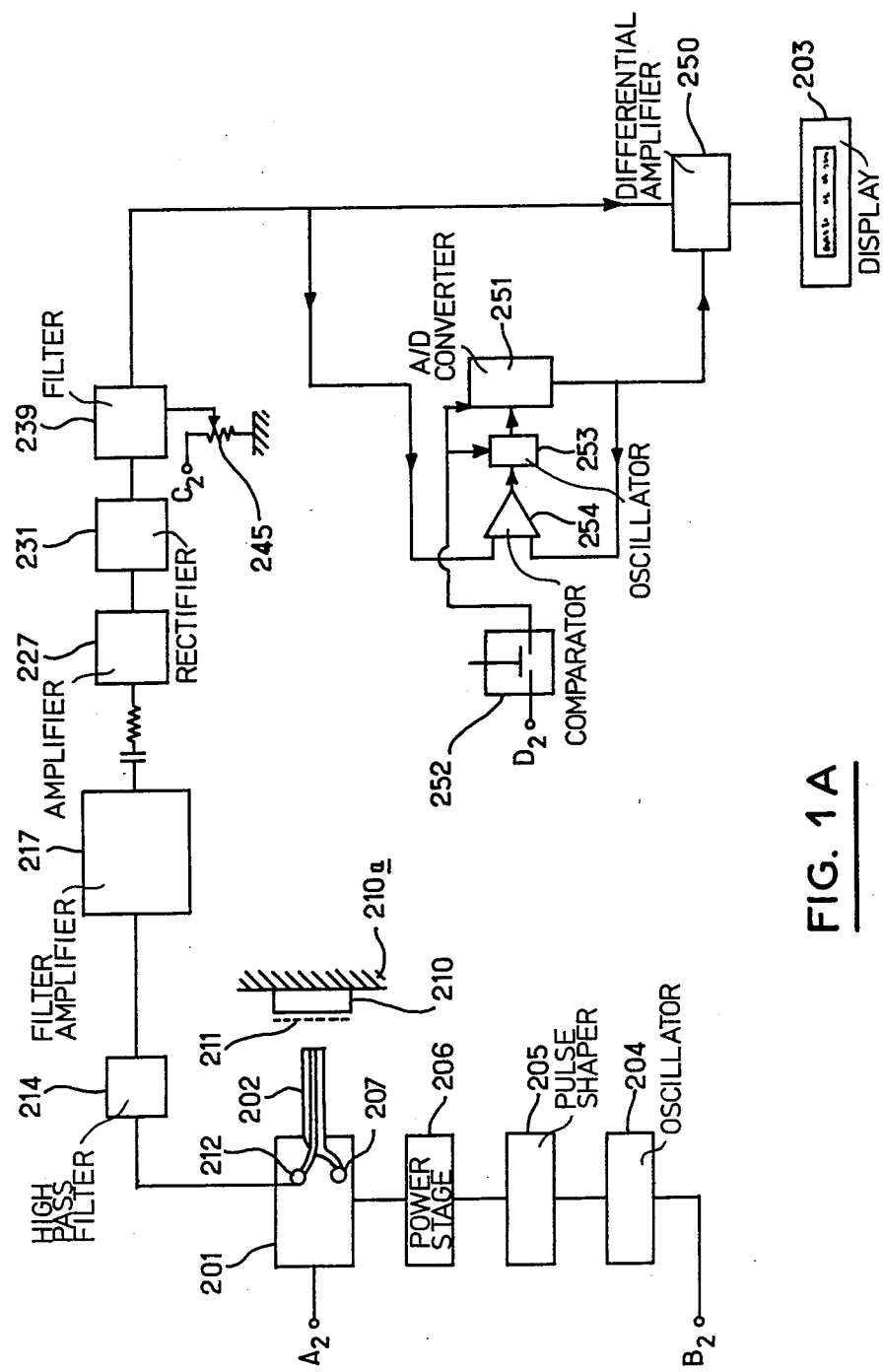
FIG. 1A shows schematically an apparatus according to a second embodiment of the invention.

FIG. 1A shows a second embodiment of the apparatus according to the invention. This apparatus has some features which are the same as those described in detail in FIG. 1 for the first embodiment. As to these common features all the numerals of FIG. 1 are increased by 100. For example, in FIG. 1A, 204 designates an oscillator, corresponding to the oscillator 104 of FIG. 1. There is a pulse shaper 205, a power stage 206, and variable resistor 209.

The various stages 214, 217, 227, 231, and 239 function in the same manner as the stages 114, 117, 127, 131 and 139 of FIG. 1, to provide an output indicative of the intensity of only the luminous flux of a frequency essentially the same as the frequency of luminous flux from photo-emitter 207, all other signals being filtered out.

In the embodiment of FIG. 1A, the power supply is connected at points $A_2$, $B_2$, $C_2$ and $D_2$.

Figure 4:
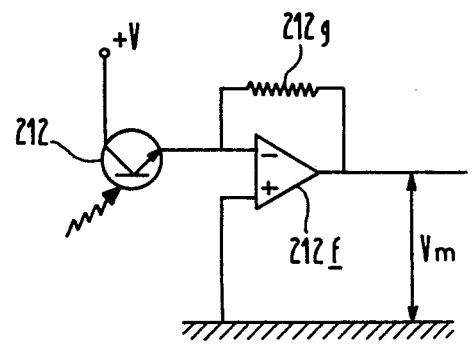

Phototransister 212 which is of the NPN type, is wired as shown on FIG. 4; the phototransistor yields a voltage $V_m$; the collector is connected to the supply voltage; there is no terminal for a base connection. The emitter is connected to the negative invertirg input of an operational amplifier 212$f$, whose other input is connected to ground. The negative input of amplifier 212$f$ is connected to its output by a resistance 212$g$ of about $10^4$ ohms; the output voltage $V_m$ of the phototransistor is taken off between the output of operational amplifier 212$f$ and ground.

When a base connection terminal of the phototransistor is provided by the builder, other types of wiring may be used than that shown on FIG. 4. In particular, in a variation shown in FIG. 2, bias resistances 212$a$, 212$b$ are placed between the supply voltage +V and ground, and their junction point is connected directly to the base. The voltage $V_m$ of the phototransistor is measured at the terminals of the resistance 212$c$ connected between the emitter and ground.

Figure 3:
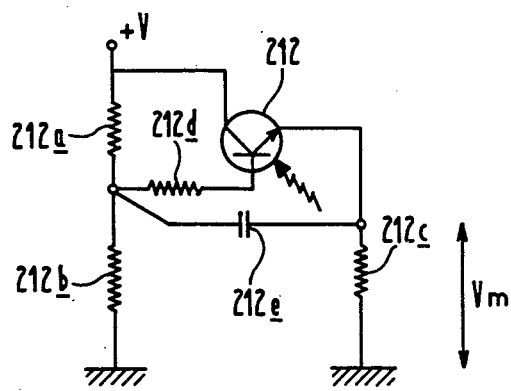

In another variation shown in FIG. 3, phototransistor 212 has its base connected to the junction point of the two bias resistances 212$a$, 212$b$ as in the preceding case and its collector is connected to the supply voltage. A resistance 212$d$, much smaller than resistances 212$a$ and 212$b$, is placed in series between the base and the junction point of bias resistances 212$a$, 212$b$. A condenser 212$e$ is connected between the emitter and the junction point of the bias resistances. The voltage $V_m$ furnished by the phototransistor is taken off at the terminals of the resistance 212$c$ connected between ground and the emitter.

Figure 2:
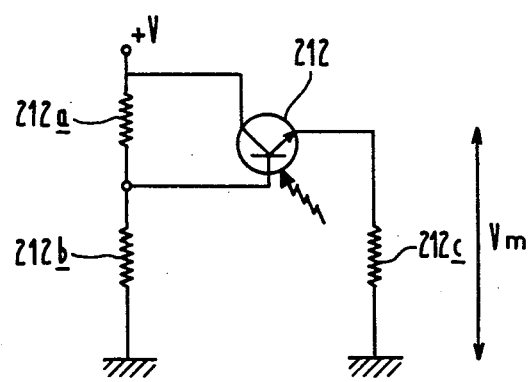
FIGS. 2–4 are circuit diagrams showing respectively three different circuit arrangements for the phototransistor of the embodiments of FIGS. 1 and 1A.

In the three circuits, shown in FIGS. 2, 3 and 4, the sensitivity or response of phototransistor 212 is held constant in spite of the variations in the ambient luminous flux received. This precaution improves the precision of the apparatus according to the invention, since the current furnished by the phototransistor is exactly proportional to the pulsed luminous flux transmitted by transparency across plate 210. The output of phototransistor 212 passes through stages 214, 217, 227, 231, and 239, as described in the embodiment of FIG. 1 for the corresponding stages. Filter stage 239 includes a supply whose voltage is regulated by means of potentiometer 245 supplied by terminal $C_2$. This regulation permits the voltages appearing at the exit of filter stage 239 to be brought to a value of less than 2.5 volts when plate 210 does not have any sebum, that is when the luminous flux received by the phototransistor 212 is at a maximum.

The voltage emitted by filter stage 239 is sent to a differential amplifier 250 by two different paths: the first path is direct; another path passes through a double analog/digital and digital/analog converter 251 (sold under the designation "AD-MC8BC" by the DATEL Company). Moreover, converter 251 outputs an analog voltage corresponding to the stored number in the memory and this analog output is connected to differential amplifier 250 which transmits the difference in voltage between its two inputs to a digital voltmeter 203. The functioning modes of converter 251 require that the input voltage be a continuous positive voltage of less than 2.5 volts, which explains the utility of the regulation obtained by variable resistance 245. The analog output voltage furnished by converter 251 is equal to the input voltage within at least about $2^{-8}$, that is, with very great precision. The output voltage corresponds to the binary number stored in the converter and thus remains constant in spite of any variations in the input voltage as long as the memory has not been instructed to register a binary number corresponding to the new entry voltage.

The loading order or signal for converter 251 is transmitted by a pushbutton 252 operated by the user. This pushbutton triggers both the return to zero or reset of the register or counter of converter 251 and, operation of an oscillator 253 which controls the loading of the counter or register consisting of the 8 bit memory of converter 251, this loading being done to establish in the memory a binary number corresponding to the input voltage from filter stage 239. A comparator 254 compares the input voltage with the output voltage of the converter, the latter corresponding to the loading of the memory. When they are equal, the comparator 254 stops oscillator 253. Thus, simply by operating pushbutton 252, the user can store in converter 251 the measuring voltage received at a given moment, and this voltage can be maintained on the corresponding input of the differential amplifier 250. If, thereafter, the measuring voltage emitted by the filter stage 239 differs from the above, differential amplifier 250 furnishes an output which is the difference between the new measuring voltage and the former one.

The circuit just described permits the automatic return to zero of the apparatus according to the invention. Actually, the user places in the apparatus a perfectly clean plate 210, not having any sebum, and presses pushbutton 252: he thus stores the measuring voltage obtained and transmits it to one of the inputs of differential amplifier 250; then the user removes plate 210, loads it with sebum on its ground side and replaces it in the apparatus: in this case, the value of the measuring voltage is modified. The differential amplifier 250 furnishes on digital voltmeter 203 the difference between the new voltage and the former one. The return to zero of the apparatus is achieved simply by pressing pushbutton 252, which eliminates all the disadvantages which occurred, when the apparatus has an unchangeable initial adjustment, from a change in the ground glass plates used, from drift in the apparatus or from poor cleaning of the plates used for the deposit of sebum.

The apparatus just described also includes all the advantages of the first embodiment; in particular, the modulation of the luminous flux emitted and the setting of the receiver on the modulation frequency free it from the influence of any parasite emissions due to ambient light or heat sources; the entire circuit of the apparatus according to the invention operates in synchronization with the flux emitter or not at all. Thus a precise and perfectly reproducible measurement is obtained without any need for isolation from the ambient environment.

It is understood that the embodiment described above is in no way limiting and all desirable modifications can be made, without going beyond the scope of the invention; in particular if, according to the nature of the plate 210 used, the response of the apparatus is not linear as a function of the quantity of sebum deposited on the plate, a device for rectifying the linearity may be added so that the response will be effectively linear. This rectifying device can in the schematic of FIG. 1A, be placed either between the differential amplifier 250 and the digital voltmeter 203, or else right at the output of filter stage 239; this use of a rectifying device allows the user to use plates made of a material other than glass, for example, sapphire, such plates permitting perfectly reproducible samples of sebum over very long periods of use.

What is claimed is:

1. Apparatus for registering the quantity of sebum secreted from a region of the skin of a living subject onto a translucent element comprising, a luminous flux emitter for directing luminous flux through a translucent element disposed in front of a reflecting surface, the translucent element being a plate having a ground surface, a receiver on the same side of the translucent element as said flux emitter for receiving the luminous flux transmitted and reflected through the translucent element by virtue of the transparency of said element, said flux emitter being modulated at a fixed frequency, and said receiver only measuring the flux received which has the frequency of modulation of the emitter, the emitter of the luminous flux comprising an electroluminescent diode, and the luminous flux receiver comprising a phototransistor, storage means for storing the value of an output voltage from the receiver resulting from a measurement of a reference specimen, said storage means comprising a digital storage unit having a register and an analog output, means for subtracting said stored value of voltage from a later output voltage of the receiver resulting from a measurement of a translucent element having sebum deposited thereon, and means for registering the value of the difference between said voltages, the storage unit including a double analog/digital and digital/analog converter with binary memory, which has an input for receiving a measuring voltage and an output for producing a reference voltage corresponding to its stored binary value, and manually operable means to reset said storage unit and to enable said unit to store a binary value corresponding to a new measuring voltage received.

2. Apparatus according to claim 1 characterized by the fact that the luminous flux emitted by the emitter is a nonmonochromatic flux.

3. Apparatus according to claim 1 characterized by the fact that the emitter of flux comprises a single element emitter of flux whose emitted flux is in a narrow range of wave lengths distributed around a median wave length, the distribution of the wave lengths around the median wave length forming essentially a Gaussian curve.

4. Apparatus according to claim 1 wherein said means for subtracting comprises a differential amplifier.

5. Apparatus according to claim 4 wherein said differential amplifier has a first input for directly receiving a measurement voltage, and a second input connected to the storage means for receiving said stored voltage.

6. Apparatus according to claim 1, wherein the means to reset the storage unit comprises means for transmitting a reset pulse to the storage unit, said pulses triggering an oscillator to load said storage unit with a number corresponding to the measuring voltage received, a comparator comparing the measuring voltage received and an output voltage of the unit corresponding to the binary value loaded in the register and blocking the oscillator when equality is attained.

7. An apparatus according to claim 6, wherein the reset pulse is furnished by a pushbutton actuated by the user.

8. An apparatus according to claim 1 wherein said means for registering comprises a digital voltmeter.

9. Apparatus according to claim 1 wherein the phototransistor has a biased base connected to ground by one resistance and to a supply voltage by another resistance, its collector being connected to the supply voltage and the measuring voltage being taken at the terminals of a resistance connected between the emitter and ground.

10. Apparatus according to claim 9, wherein a common junction of the two bias resistances is connected to the base by a resistance which is much smaller than the two resistances, and the common junction is connected to the emitter by a condenser.

11. Apparatus according to claim 1, wherein the phototransistor has its collector connected to a supply and its emitter connected to the negative inverting input of an operational amplifier whose other input is connected to ground, said inverting input being connected to the output of the operational amplifier by a resistance, the output voltage being taken at the output of the operational amplifier.

12. Apparatus according to claim 1, characterized by the fact that it includes two co-axial optical fibers, of which one end is connected to an emitter-receiver unit for luminous flux and of which the other end is placed facing a ground glass plate applied against a flat mirror.

* * * * *